(12) United States Patent
Cridge et al.

(10) Patent No.: US 11,761,939 B1
(45) Date of Patent: Sep. 19, 2023

(54) MODULAR HEALTH EXPOSURE SENSOR SYSTEM

(71) Applicant: Cornerstone Research Group, Inc., Miamisburg, OH (US)

(72) Inventors: Mark C. Cridge, Miamisburg, OH (US); Trang T. Young, Dayton, OH (US); Matthew S. Benefiel, Xenia, OH (US); Eric A. Nees, Beavercreek, OH (US); Brian E. Henslee, Galloway, OH (US)

(73) Assignee: Cornerstone Research Group, Inc., Miamisburg, OH (US)

( * ) Notice: Subject to any disclaimer, the term of this patent is extended or adjusted under 35 U.S.C. 154(b) by 295 days.

(21) Appl. No.: 17/161,842

(22) Filed: Jan. 29, 2021

Related U.S. Application Data

(60) Provisional application No. 62/967,656, filed on Jan. 30, 2020.

(51) Int. Cl.
 *G01N 33/00* (2006.01)
 *G06F 13/42* (2006.01)
 (Continued)

(52) U.S. Cl.
 CPC ....... *G01N 33/0073* (2013.01); *G01N 33/004* (2013.01); *G01N 33/0037* (2013.01);
 (Continued)

(58) Field of Classification Search
 CPC ........... G01N 33/0073; G01N 33/0037; G01N 33/004; G01N 33/0044; G01N 33/0047;
 (Continued)

(56) References Cited

U.S. PATENT DOCUMENTS 7,743,187 B2   6/2010  Choi et al.
8,731,372 B2   5/2014  Ochiai et al.
 (Continued)

FOREIGN PATENT DOCUMENTS

AU   2020102451 A4 * 11/2020
CN   109270873 A  *  1/2019  ............. G01D 21/02
 (Continued)

OTHER PUBLICATIONS

CN-109270873-A-English (Year: 2019).*
 (Continued)

*Primary Examiner* — Kristina M Deherrera
*Assistant Examiner* — Fatemeh Esfandiari Nia
(74) *Attorney, Agent, or Firm* — DINSMORE & SHOHL LLP

(57) ABSTRACT

A health exposure sensor system includes a housing, a monitoring platform in the housing, and a power source. The monitoring platform includes at least one modular gas sensor, a circuit board having a microcontroller, and data ports for connecting the modular gas sensor to the circuit board. The housing includes manifolds to direct atmospheric air to the modular gas sensor. The modular gas sensor includes a gas detector and a gas sensor circuit board having a gas sensor microcontroller. The gas sensor microcontroller includes at least one on-chip universal asynchronous receiver-transmitter peripheral and at least one on-chip USB peripheral, where both peripherals include input/output functionality and are connected to a single data port interface for external communication. An associated method of operating the same includes selectively enabling individually either the UART peripheral or the USB peripheral via digital I/O configuration of the microcontroller.

21 Claims, 10 Drawing Sheets

(51) Int. Cl.
*G16H 40/67* (2018.01)
*G01S 19/42* (2010.01)
*G06F 3/0484* (2022.01)
*G08C 17/02* (2006.01)

(52) U.S. Cl.
CPC ..... *G01N 33/0044* (2013.01); *G01N 33/0047* (2013.01); *G01N 33/0054* (2013.01); *G01N 33/0062* (2013.01); *G06F 13/4282* (2013.01); *G16H 40/67* (2018.01); *G01S 19/42* (2013.01); *G06F 3/0484* (2013.01); *G06F 2213/0042* (2013.01); *G08C 17/02* (2013.01)

(58) Field of Classification Search
CPC ............ G01N 33/0054; G01N 33/0062; G06F 13/4282; G06F 3/0484; G06F 2213/0042; G16H 40/67; G01S 19/42; G08C 17/02
See application file for complete search history.

(56) References Cited

U.S. PATENT DOCUMENTS

| | | | |
|---|---|---|---|
| 9,710,414 | B2 | 7/2017 | Liang et al. |
| 10,673,280 | B2 | 6/2020 | Raj et al. |
| 2002/0178789 | A1* | 12/2002 | Sunshine ............ G01N 33/0009 73/31.06 |
| 2011/0201382 | A1 | 8/2011 | Hsiao |
| 2016/0202224 | A1* | 7/2016 | Lloyd ...................... G05D 7/01 73/865.8 |
| 2016/0305797 | A1* | 10/2016 | Pietrasik ................. H04W 4/80 |
| 2018/0120279 | A1* | 5/2018 | Yi ...................... G01N 33/0075 |
| 2019/0228631 | A1 | 7/2019 | Stinson et al. |
| 2019/0356841 | A1 | 11/2019 | Lee et al. |
| 2021/0047174 | A1* | 2/2021 | Katginari .................. B81B 7/04 |
| 2022/0311273 | A1* | 9/2022 | Field, III .................. H02J 7/35 |

FOREIGN PATENT DOCUMENTS

| | | | |
|---|---|---|---|
| KR | 200329462 Y | 10/2003 | |
| KR | 20090007892 A | 1/2009 | |
| WO | 2019101884 A1 | 5/2019 | |
| WO | WO-2020005431 A1 * | 1/2020 | ............. G01D 11/24 |

OTHER PUBLICATIONS

Murray "Module Combines Multiple Sensors in a Tiny Package" https://www.designnews.com/electronics-test/module-combines-multiple-sensors-tiny-package/133285556057894, Dec. 1, 2017, 8 pgs.

* cited by examiner

MODULAR HEALTH EXPOSURE SENSOR SYSTEM

CROSS-REFERENCE TO RELATED APPLICATIONS

This application claims priority to U.S. Provisional Application 62/967,656, filed Jan. 30, 2020, which is incorporated by reference herein in its entirety.

STATEMENT REGARDING FEDERALLY SPONSORED RESEARCH OR DEVELOPMENT

This invention was made with U.S. Government support under Contract No. FA8650-19-C-6019 awarded by the U.S. Air Force Materiel Command to Cornerstone Research Group Inc. The U.S. Government has certain rights in the invention.

TECHNICAL FIELD

Embodiments of the present disclosure generally relate to health exposure sensor systems for monitoring exposure to airborne contaminants in the form of one or more of gases, vapors, and particulate matters that are part of an air mixture but are foreign to the normal and pure state of the mixture.

BACKGROUND

Breathing air quality can have a profound impact on an individual's health. A variety of common volatile organic compounds (VOCs) and some air contaminants have been shown to cause varying health effects ranging from headaches to stroke, heart attack or cancer. More specific or uncommon air quality hazards are present based on occupational duties that can have similar or more severe consequences. Individuals have varying air quality exposure through personal choices at home and occupational hazards at work and the sum of these exposures represents an individual's Total Exposure Health (TEH). The ability to monitor TEH helps medical professionals and employers manage individual's health in view of their specific lifestyle. The ability to monitor TEH also helps medical professionals and employers optimize health and performance for occupational and personal needs.

However, current sensor packages to provide data related to TEH involve custom hardware specific to a distinct monitoring environment and individual making them costly and difficult to adapt to changing lifestyles and changing occupational conditions. Typically, once a set of sensors are selected, supporting sensor equipment is designed around that single set of sensors without any way to change or adapt sensor types for a different application. Providing a system with a vast array of sensors to handle every scenario in a "one size fits all" solution is also impractical due to size and resource limitations. Equipment should be compact and wearable in a way that doesn't interfere with an individual's mobility or duties. A compact base set of hardware that supports a bank of adaptable and interchangeable sensor modules for TEH monitoring is needed.

SUMMARY

As such, there are needs for modular health exposure systems which supports a bank of adaptable and interchangeable sensor modules for TEH monitoring. Further, the need continues for such systems which are compact and wearable in a way that doesn't interfere with an individual's mobility or duties. The present disclosure provides a modular health exposure system that is configured to allow for the ready exchange of sensor modules to adapt the modular health exposure system to changing lifestyles and changing occupational conditions.

Embodiments of the present disclosure relate to a health exposure sensor system. The system includes a housing, a monitoring platform disposed in the housing, and a power source. Further, the monitoring platform comprises at least one modular gas sensor, a circuit board comprising a microcontroller, and an array of data ports for connecting the at least one modular gas sensor to the circuit board. The housing comprises one or more manifolds to direct air flow from the atmosphere surrounding the housing to the at least one modular gas sensor. The modular gas sensor comprises a gas detector enclosed in a sensor housing with an opening for gas diffusion to the gas detector and a gas sensor circuit board comprising a gas sensor microcontroller. The gas sensor microcontroller comprises at least one on-chip universal asynchronous receiver-transmitter (UART) peripheral and at least one on-chip USB peripheral, wherein both the UART peripheral and the USB peripheral comprise input/output (I/O) functionality and are connected to a single data port interface for communication external to the modular gas sensor.

Embodiments of the present disclosure relate to a method of operating a health exposure sensor system. The health exposure sensor system includes a monitoring platform which comprises at least one modular gas sensor, a circuit board comprising a microcontroller, and an array of data ports for connecting the at least one modular gas sensor to the circuit board. Further, the modular gas sensor includes a gas detector enclosed in a sensor housing with an opening for gas diffusion to the gas detector and a gas sensor circuit board comprising a gas sensor microcontroller. The gas sensor microcontroller includes at least one on-chip universal asynchronous receiver-transmitter (UART) peripheral and at least one on-chip USB peripheral, wherein both the UART peripheral and the USB peripheral comprise input/output (I/O) functionality and are connected to a single data port interface for communication external to the modular gas sensor. The method includes selectively enabling individually either the UART peripheral or the USB peripheral via digital I/O configuration of the gas sensor microcontroller.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
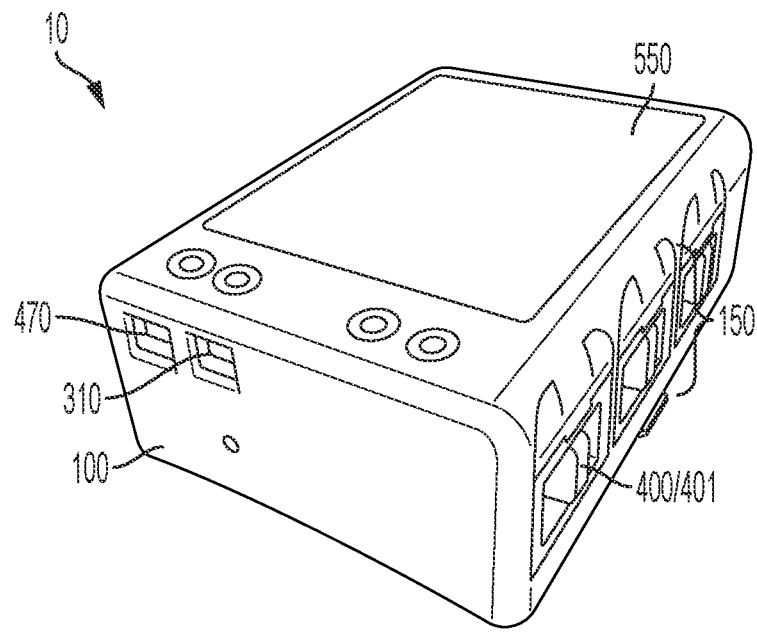
FIG. 1A is an illustration of a health exposure sensor system in accordance with one or more embodiments of the present disclosure.

Embodiments of the present disclosure generally relate to a health exposure sensor system. The health exposure sensor system incorporates a shared or common hardware platform that supports a customizable bank of air quality sensor modules. This flexibility allows the user to customize and field a limited monitoring system for wearable applications where only a very compact solution is feasible, or scale up the system to incorporate multiple sensor modules to gather a greater amount of information. Such a system can accommodate a preprogramed database of sensor modules that can be identified and activated upon connection to one of a plurality of connection ports.

In accordance with embodiments of a health exposure sensor system 10 and with reference to FIGS. 1A, 1B, 2A, and 2B, the system 10 comprises a housing 100, a monitoring platform 200 disposed in the housing 100, and a power source 300. Further, the monitoring platform 200 comprises at least one modular gas sensor 400, a circuit board 210 comprising a microcontroller 220, and an array of data ports 230 for connecting the at least one modular gas sensors 400 to the circuit board 210. The housing 100 comprises one or more manifolds 110 to direct air flow from the atmosphere surrounding the housing 100 to the at least one modular gas sensor 400. Additionally, the modular gas sensor 400 comprise a gas detector 410 enclosed in a sensor housing 420 with an opening 430 for gas diffusion to the gas detector 410 and a gas sensor circuit board 440 comprising a gas sensor microcontroller 450. The gas sensor microcontroller 450 additionally comprises at least one on-chip universal asynchronous receiver-transmitter (UART) peripheral 452 and at least one on-chip USB peripheral 454. It is noted that both the UART peripheral 452 and the USB peripheral 454 comprise input/output (I/O) functionality and are connected to a single data port interface 460 for communication external to the modular gas sensor 400.

Having generally described the various components of the health exposure sensor system 10, each component and sub-system will be described in further detail. As previously indicated and with reference to FIGS. 2A, 2B, 3A, and 3B, the monitoring platform 200 includes at least one modular gas sensor 400, a circuit board 210 comprising a microcontroller 220, and an array of data ports 230 for connecting the at least one modular gas sensor 400 to the circuit board 210. The monitoring platform 200 is provided as the operational center of the health exposure sensor system 10. The monitoring platform 200 is disposed within the housing 100 for containment and protection of the components of the monitoring platform 200 as well as to provide a user-friendly form to the health exposure sensor system 10.

The modular gas sensors 400 of the health exposure sensor system 10 are based around detector devices that are configured to accomplish detection of a range of air quality contaminants in the Occupational Safety and Health Administration (OSHA) Permissible Exposure Limit (PEL) ranges. Based on the desire to maintain a compact wearable design, in various embodiments, the modular gas sensors 400 may include electrochemical, catalytic, infrared, or semiconductor sensing methods.

In one or more embodiments, the modular gas sensors 400 may include sensors configured to detect and/or quantify one or more gaseous species. In various embodiments, the gaseous species appraised by the modular gas sensors 400 may include one or more of oxygen ($O_2$), volatile organic compounds (VOC), carbon dioxide ($CO_2$), carbon monoxide (CO), ammonia ($NH_3$), hydrogen cyanide (HCN), methane ($CH_4$), nitrogen oxides ($NO_x$), and hydrogen sulfide ($H_2S$). Example VOCs include acetone, alcohols, formaldehyde, methylene chloride, toluene, isobutylene.

In one or more embodiments, the health exposure sensor system 10 includes one or more ancillary sensor modules 401 communicatively connected with the monitoring platform 200. The ancillary sensor modules 401 represent sensor platforms configured to monitor atmospheric parameters beyond those monitored by the at least one modular gas sensor 400. It will be appreciated that in one or more embodiments, the ancillary sensor modules 401 are in fluid communication with the one or more manifolds 110 provided in the housing 100 to direct airflow from the atmosphere surrounding the housing 100 to the ancillary sensor modules 401. In various embodiments, the one or more ancillary sensor modules 401 may be selected to include sensors configured to monitor one or more of atmospheric sound intensity, radiation, temperature, pressure, and humidity.

In one or more embodiments, the ancillary sensor modules 401 interface with the circuit board 210 of the monitoring platform 200 via one or more of the data ports 230 provided on the monitoring platform 200. Such arrangement allows the ancillary sensor modules 401 to be interchanged to provide specific ancillary sensor modules 401 configured to monitor environmental parameters of interest in the particular occupational setting of deployment or lifestyle of the user.

In one or more embodiments, one or more of the ancillary sensor modules 401 may interface with the circuit board 210 of the monitoring platform 200 with a direct connection to the circuit board 210. For example, the ancillary sensor module 401 may be soldered directly to the circuit board 210 to provide a permanent connection. It will be appreciated that such direct connection reduces the complexity and improves the durability of the connection when deploying an ancillary sensor module 401 anticipated to be utilized for all deployments of the health exposure sensor system 10. Additionally, such direct connection removes the need to occupy one of the data ports 230, freeing such data port 230 for connection with a modular gas sensor 400 or an ancillary sensor module 401.

It will be appreciated that inclusion of the ancillary sensor modules 401 within the operational package of the health exposure sensor system 10 alleviates the need for deployment and transport of a multiplicity of sensing equipment. As such, the health exposure sensor system 10 may reduce the total weight, the total volume, and/or the total cost of monitoring the full breath of desired parameters for a given occupational setting. For example, traditionally a standalone gas monitor and a standalone particulate monitor may be deployed with each monitor requiring an independent user interface, power supply, housing, communication protocol, and maintenance procedure. The advancement of the present system with the integrated utilization of the modular gas sensors 400 and the ancillary sensor modules 401 within the operational package of the health exposure system 10 allows for the full breadth of desired parameters to be consistently monitored without transporting multiple units or settling for inconsistent monitoring with monitoring units (for example, the modular gas sensors 400 and the ancillary sensor modules 401) swapped out in a serial manner to capture snapshots of each desired parameter.

In one or more embodiments and with reference to FIGS. 4, 5A, 5B, and 5C, the various sensor modules such as the modular gas sensors 400 and other ancillary sensor modules 401 may comprise a sensing unit and a microcontroller with associated circuitry all housed within an enclosure with a hole that allows passage of the air or gases to the sensing unit. For example, the modular gas sensor 400 may comprise a gas detector 410 enclosed in a sensor housing 420 with an opening 430 for gas diffusion to the gas detector 410 as well as a gas sensor circuit board 440 comprising a gas sensor microcontroller 450. It will be appreciated that each of the ancillary sensor modules 401 may have the same or similar construction with an ancillary sensing unit 411 enclosed in a sensor housing 420 with an opening 430 for diffusion of air to the ancillary sensing unit 401 as well as an ancillary sensing unit circuit board 441 comprising an ancillary sensor microcontroller 451 to control the same.

In one or more embodiments, the modular gas sensors 400 comprise electrochemical canister-shaped sensors as the gas detector 410. In various embodiments, such gas detectors 410 may be sensitive to the detection of gases of less than 100 parts per million (ppm), less than 1 ppm, less than 100 parts per billion, less than 10 ppb, or less than 1 ppb.

In one or more embodiments, the health exposure sensor system 10 includes a particulate sensor module 402 communicatively connected with the monitoring platform 200. The particulate sensor module 402 represents a sensor platform configured to monitor particulates in the atmosphere surrounding the health exposure sensor system 10.

In one or more embodiments, the particulate sensor module 402 interfaces with the circuit board 210 of the monitoring platform 200 via a particulate sensor connector 470 provided on the circuit board 210 monitoring platform 200. The particulate sensor module 402 may be provided as a separate unit affixed exterior to the housing 100 of the health exposure sensor system 10. Specifically, the particulate sensor module 402 may connect to the particulate sensor connector 470 through an orifice provided in the housing 100 of the health exposure sensor system 10 and secured to an exterior face of the housing 100 to provide particulate monitoring of the surrounding atmosphere. Such arrangement allows the particulate sensor module 402 to be interchanged to provide monitoring of particulates of a specific type, size, or makeup of interest in the particular occupational setting of deployment or lifestyle of the user. It will be appreciated that in one or more embodiments, the particulate sensor module 402 may alternatively be provided on the interior of the housing 100 with the same or similar orifice provided in the housing 100 to allow the particulate sensor module 402 to directly sample the atmosphere surrounding the health exposure sensor system 10.

In various embodiments, the particulate sensor module 402 may be selected to provide monitoring of particulate sizes ranging from 10 nanometers (nm) to 20 micrometers (μm), 10 nm to 10 μm, 10 nm to 5 μm, 100 nm to 20 μm, 500 nm to 20 μm, and 350 nm to 12.5 μm. In one or more embodiments, the particulate sensor module 402 may be an optical particle counter. An optical particle counter operates by providing a sensor and a beam of light, such as a laser, which sit at an angle to each other. As a particle passes in front of the light, some light is reflected towards the sensor and the sensor registers a pulse for as long as the particle reflects light to the sensor. If the air is moving at a consistent speed, the length of this pulse can be used to estimate the particle's diameter. An example particulate sensor module 402 is the commercially available OFC-R1 (Alphasense Air, United Kingdom).

In one or more embodiments, the gas sensor circuit board 440 and/or the ancillary sensing unit circuit board 441 may be formed from two or more separate circuit boards connected by pins 442. For example, the gas detector 410 or the ancillary sensing unit 411 may be affixed to a first circuit board and the gas sensor microcontroller or ancillary sensor microcontroller 451 as well as the data port interface 460 may be affixed to a second circuit board, the first circuit board and the second circuit board collectively forming the gas sensor circuit board 440 or the ancillary sensing unit circuit board 441. Further, in one or more embodiments, the gas sensor circuit board 440 and/or the ancillary sensing unit circuit board 441 may comprise a status light 454, such as a light emitting diode (LED), to indicate the operating or power status of the gas sensor circuit board 440 or the ancillary sensing unit circuit board 441.

In one or more embodiments, the various sensor modules such as the modular gas sensors 400 and ancillary sensor modules 401 each output a modulated current or voltage signal indicative of the magnitude of the measured or sensed parameter. For example, the modular gas sensor 400 may output a modulated current or voltage signal indicative of the presence of an air quality contaminant in the atmosphere surrounding the housing 100. Similarly, one of the ancillary sensor modules 401 may output a modulated current or voltage signal indicative of the humidity, temperature, pressure, and/or sound intensity within the atmosphere surrounding the housing 100. In one or more embodiments, the modulated current or voltage signal may be generated directly by the gas detector 410 or the ancillary sensing unit 411. In further embodiments, the gas sensor microcontroller 450 or ancillary sensor microcontroller 451 may manipulate the direct outputs of the gas detector 410 or the ancillary sensing unit 411 respectively to generate the modulated current or voltage signal output by the modular gas sensor 400 or ancillary sensor module 401.

In one or more embodiments, the health exposure sensor system includes a global positioning system (GPS) 500 as an ancillary sensor module 401 configured to correlate data received from the modular gas sensors 400 and/or other ancillary sensor modules 401 with the geospatial location where sampling occurred. In some embodiments, the GPS 500 may be provided as an embedded or integral part of the monitoring platform 200 with direct connection to the circuit board 210. In further embodiments, the GPS 500 may be provided as an ancillary sensor module 401 which may be reversibly deployed and removed from the health exposure sensor system 10. In such embodiments, the GPS 500 may interface with the circuit board 210 of the monitoring platform 200 via one or more of the data ports 230 provided on the monitoring platform 200. It will be appreciated that it may be desirable to remove the GPS 500 from the health exposure sensor system 10 to extend the battery life of the health exposure sensor system 10 or if geospatial location data does not provide useful insights with regards to the deployed objective of the health exposure sensor system 10.

The circuit board 210 provided as a component of the monitoring platform 200 serves to support and electrically connect the various components of the monitoring platform 200. Specifically, and with reference to FIGS. 3A and 3B, the microcontroller 220 and the array of data ports 230 are electrically connected to the circuit board 210 to allow transmission of data in the form of electrical signals between the modular gas sensors 400 and other ancillary sensor modules 401, the microcontroller 220, and other system components such as a data storage module 700. The specification and operation of the circuit board 210 may be in accordance with other circuit boards commonly known to those skilled in the art. Specifically, the circuit board 210 may comprise a printed circuit board which mechanically supports and electrically connects the components of the monitoring platform 200 using conductive tracks etched from one or more sheet layers of copper laminated onto and/or between sheet layers of a nonconductive substrate. It will be appreciated that one skilled in the art would be familiar with connection of the various components of the monitoring platform 200 to the circuit board 210 such as via soldering the components onto the circuit board 210 to both electrically connect and mechanically fasten them to it.

One of the specific components affixed to the circuit board 210 is the array of data ports 230 for connecting the at least one modular gas sensor 400 and other ancillary sensor modules 401 to the circuit board 210. The data ports 230 serve as universal receptacles capable of allowing for connection and swapping of various sensor modules such as the modular gas sensors 400 and other ancillary sensor modules 401. As the modular gas sensors 400 and other ancillary sensor modules 401 desirously communicate with the microcontroller 220, the data ports 230 may be capable of forming a data transfer connection between the microcontroller 220 and the modular gas sensors 400 and other ancillary sensor modules 401. In one or more embodiments, the data ports 230 include a universal serial bus (USB) type connector to allow for both electrical and mechanical connection. It will be appreciated that the present disclosure is not limited to USB type connectors, but discussion of USB type connectors is merely provided as an example of one of a multiplicity of standard connector types utilized in electronic devices worldwide. Example connector types include USB A-Type, USB B-Type, USB C-Type, Mini USB B, Micro USB B, FireWire (IEEE 1394), Thunderbolt, eSATA, SATA, and RJ45.

Figure 6:
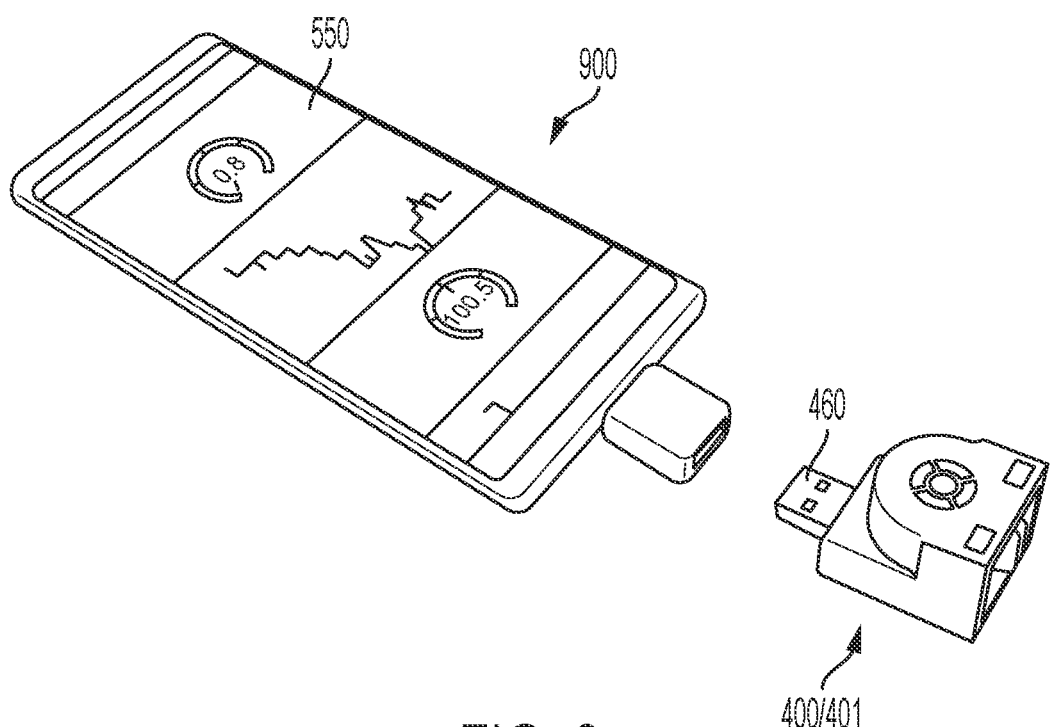
FIG. 6 is an illustration of a sensor unit positioned for connection to an external computing device in accordance with one or more embodiments of the present disclosure.

In various embodiments, the modular gas sensors 400 and other ancillary sensor modules 401 include connectors configured to mate with the connector type of the data ports 230 provided on the monitoring platform 200. These connectors may be referenced as a data port interface 460. It will be appreciated that inclusion of the data port interface 460 as a component of the modular gas sensors 400 and other ancillary sensor modules 401 allows the modular gas sensors 400 and ancillary sensor modules 401 to be removed from the data port 230 of the monitoring platform 200 and connected to a corresponding port of the same type on a computing device 900. With reference to FIG. 6, a sensor unit 400/401 is illustrated positioned for connection with an example computing device 900. Such operation allows the computing device 900 to power the modular gas sensor 400 and/or other ancillary sensor module 401 via connection with the data port interface 460 and access a real-time readout of measurements by the modular gas sensor 400 and/or other ancillary sensor module 401. For example, the data port interface 460 may be a USB connection allowing the modular gas sensor 400 and the data ports 230 to communicatively connect the modular gas sensor 400 such that the modular gas sensor 400 is operable to be removed from the data port 230 of the monitoring platform 200 and connected to a USB port of a computing device 900. It will be appreciated that connection of a computing device 900 and the modular gas sensor 400 at the data port interface 460 may allow the computing device 900 to power the modular gas sensor 400 via the USB port serving as the data port interface 460 and access a real-time readout of measurements by the modular gas sensor 400.

In one or more embodiments, the circuit board 210 includes a programming port 320. The programming port 320 provides a connection to the circuit board 210 to allow for communicative linkage with the various components of the monitoring platform 200 to allow for completion of calibration, updates, or other programming functionality.

The monitoring platform 200 further includes the microcontroller 220 as a component of the circuit board 210. The microcontroller 220 employs a custom communication protocol to allow it to communicate with the multiplicity of modular gas sensors 400 and/or ancillary sensor modules 401 which may use different communication protocol as well as computing devices 900 and/or other hardware external to the health exposure sensor system 10. Specifically, the microcontroller 220 acts as an interpreter between the modular gas sensors 400 and other ancillary sensor modules 401 and other hardware components of the health exposure sensor system 10 for operations. Further details regarding the various communication protocols and managing switching between such communication protocols is provided infra.

The health exposure sensor system 10 includes the housing 100 with the monitoring platform 200 disposed in the housing 100. The housing 100 provides protection to the monitoring platform 200 and a user-friendly form to the health exposure sensor system 10. In one or more embodiments and with reference to FIGS. 1A and 1B, the housing 100 is formed from a base 120 configured for securement of the monitoring platform 200 and a lid 130 configured to mate with the base 120. The base 120 may be configured to secure the circuit board 210, and the selected sensor units 400/401 connected to the array of data ports 230 on the circuit board 210. It will be appreciated that the power source 300 may be secured to the base 120 or the lid 130 of the housing 100 in various embodiments.

Figure 1B:
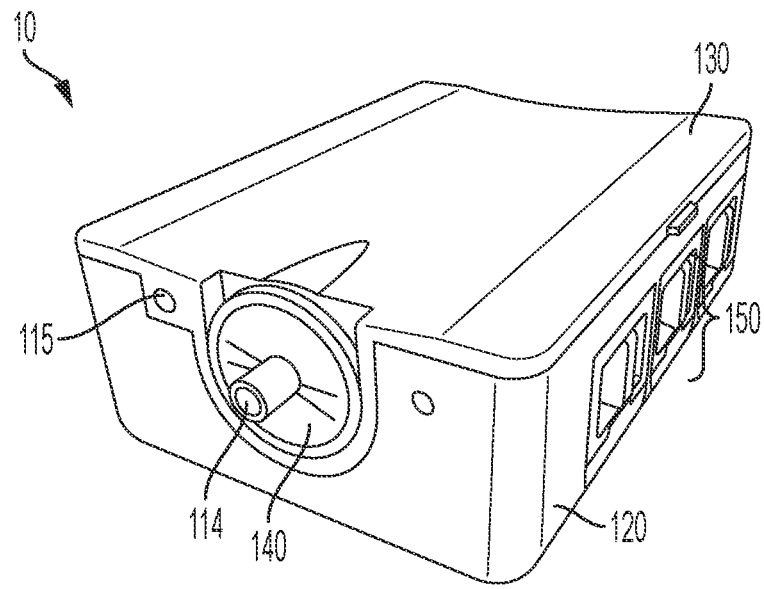
FIG. 1B is an illustration of the reverse of FIG. 1A.
Figure 2A:
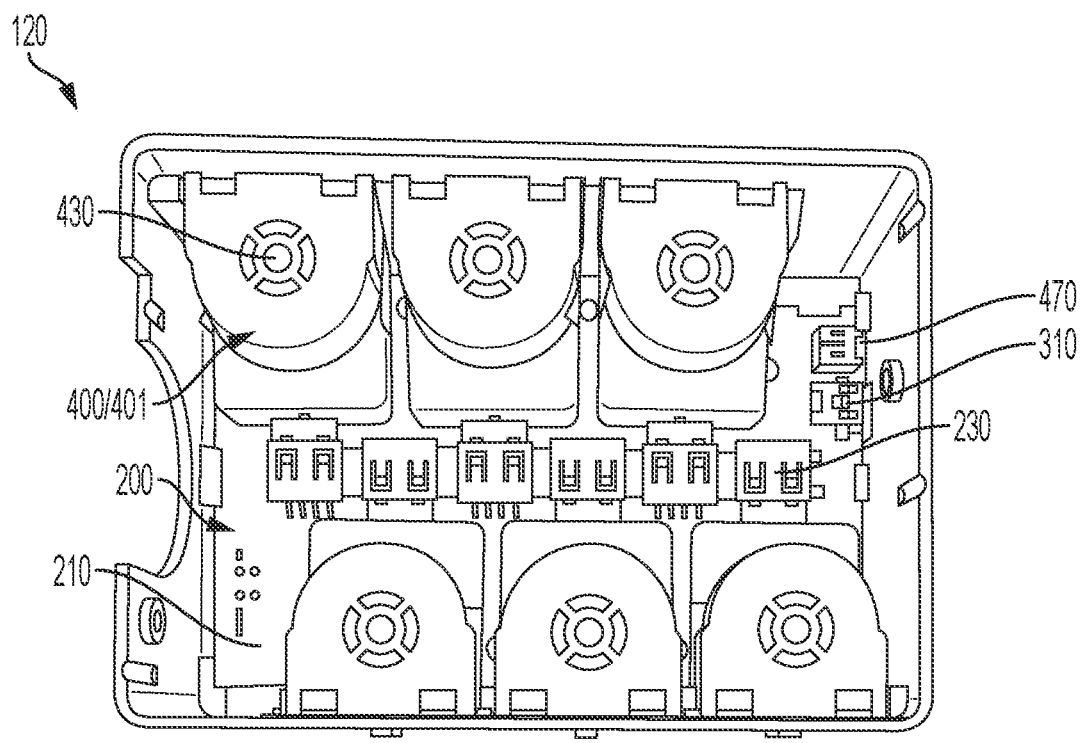
FIG. 2A is an illustration of the interior of a health exposure sensor system in accordance with one or more embodiments of the present disclosure.
Figure 2B:
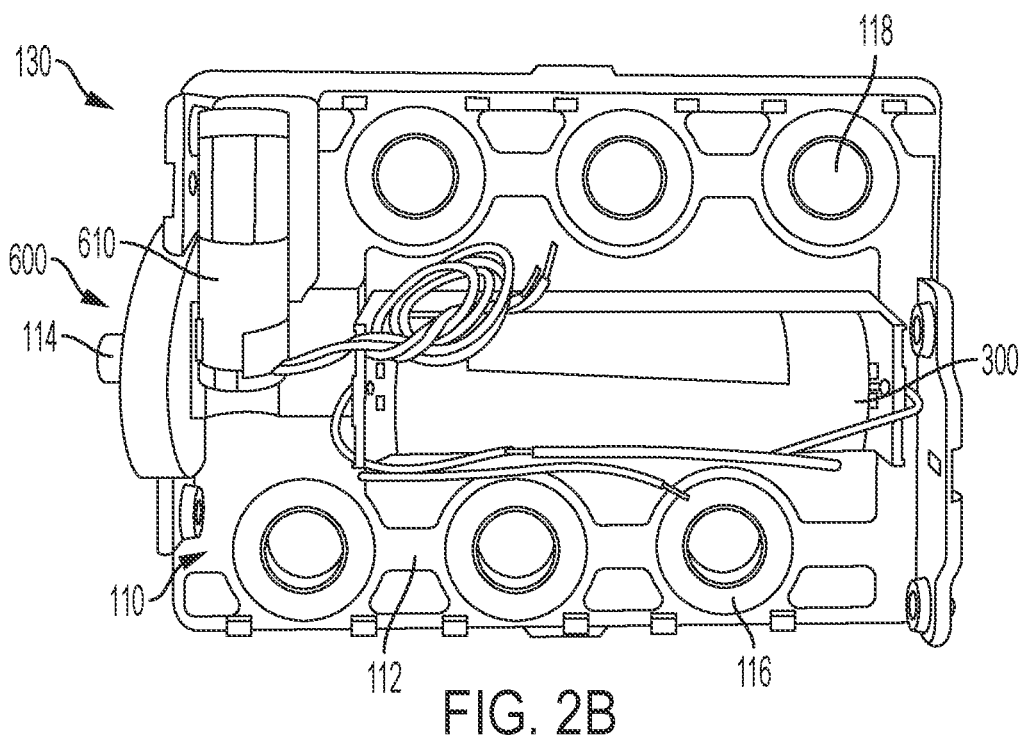
FIG. 2B is an illustration of the interior of a health exposure sensor system in accordance with one or more embodiments of the present disclosure.
Figure 3A:
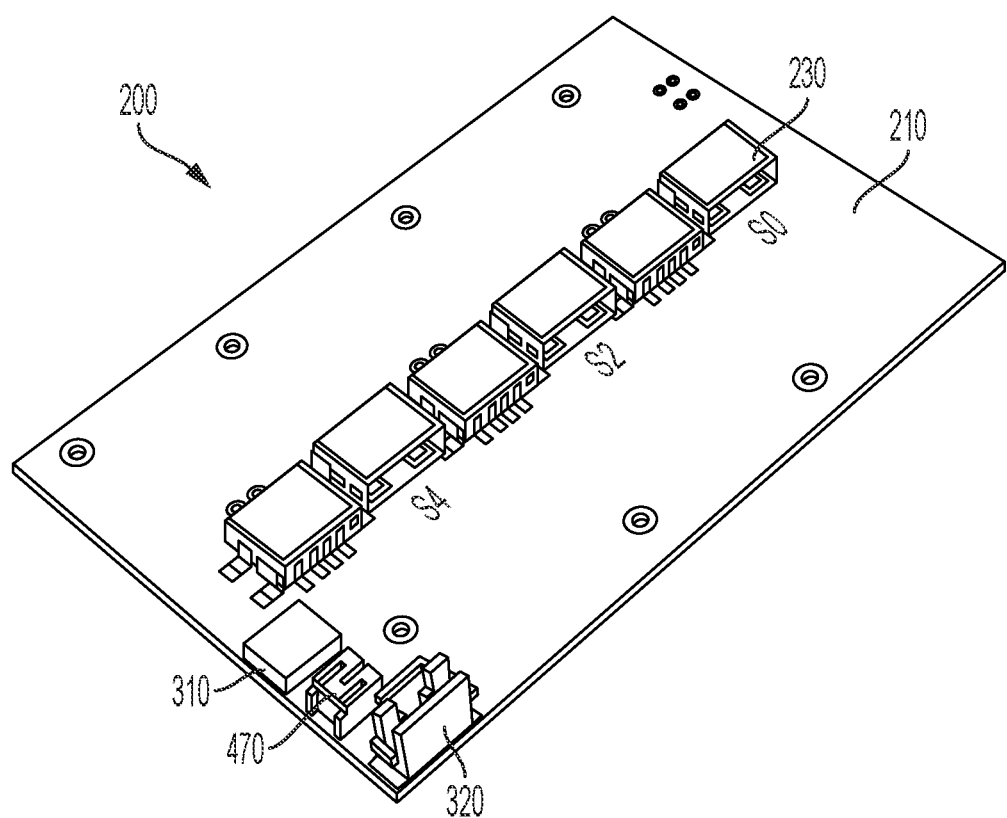
FIG. 3A is an illustration of the monitoring platform of a health exposure sensor system in accordance with one or more embodiments of the present disclosure.
Figure 3B:
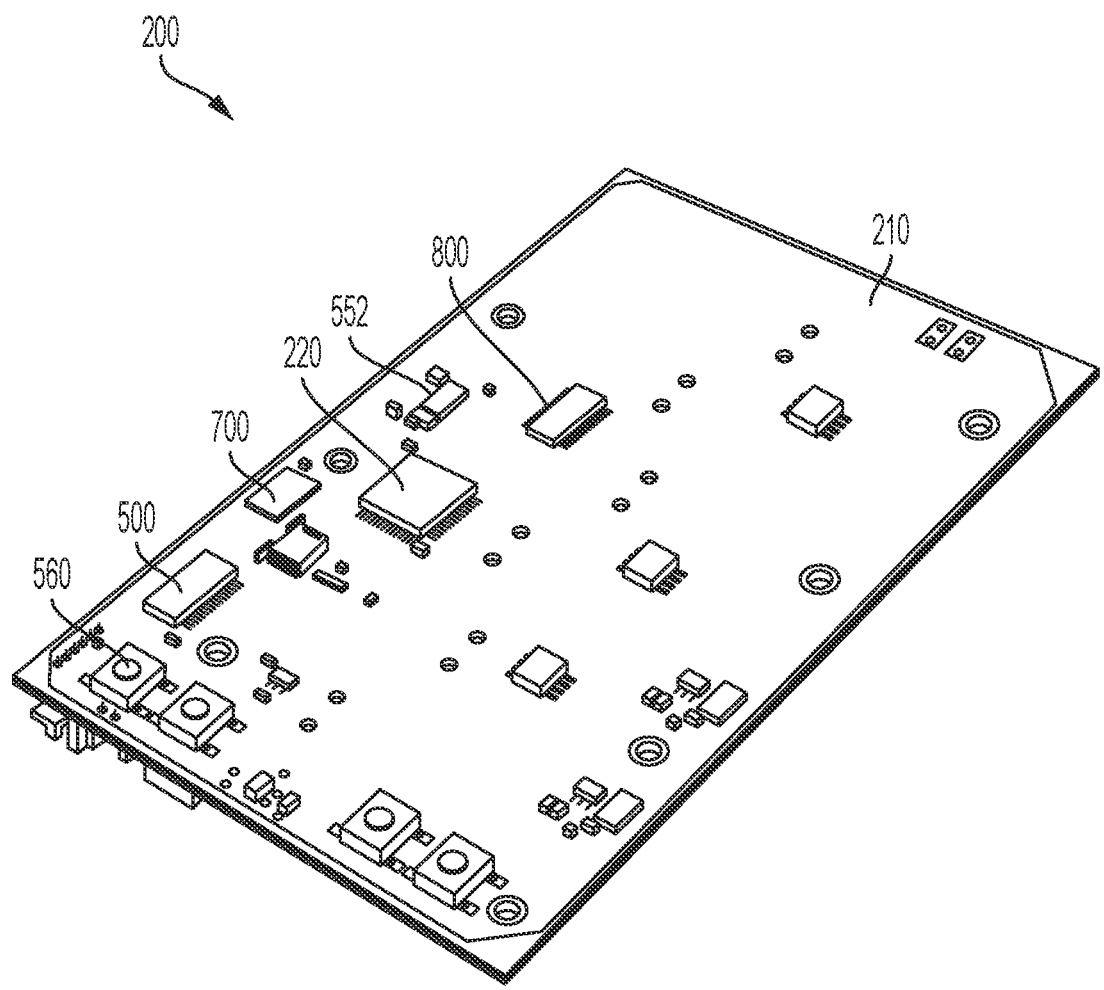
FIG. 3B is an illustration of the reverse of FIG. 3A.
Figure 4:
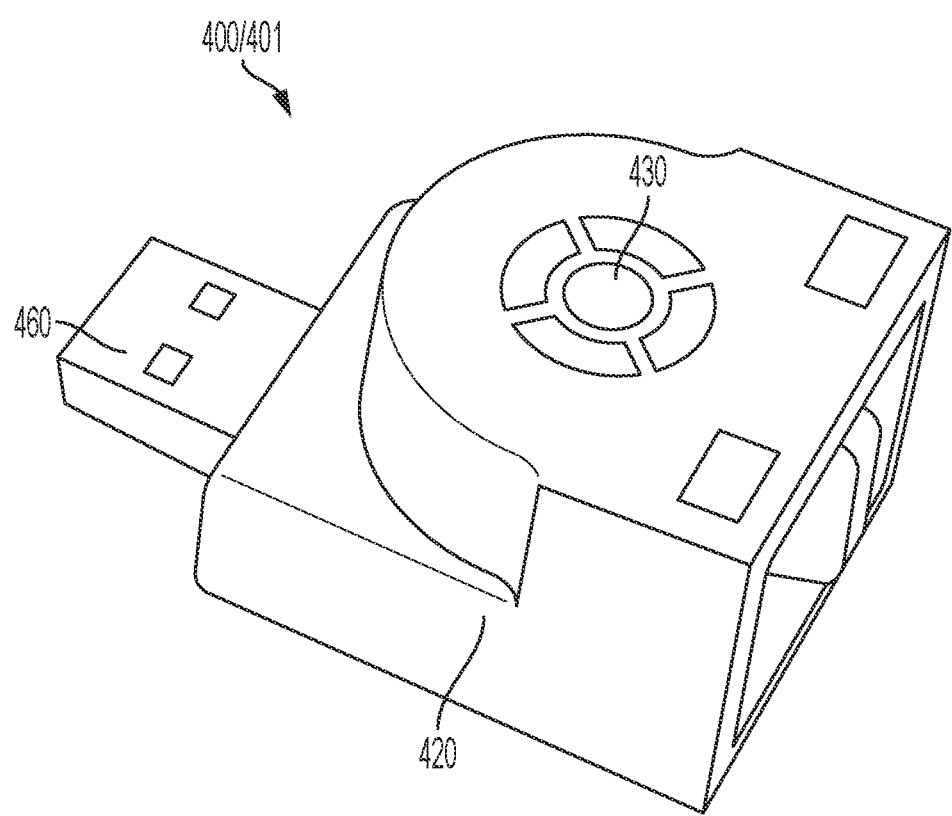
FIG. 4 is an illustration of a sensor unit in accordance with one or more embodiments of the present disclosure.
Figure 5A:
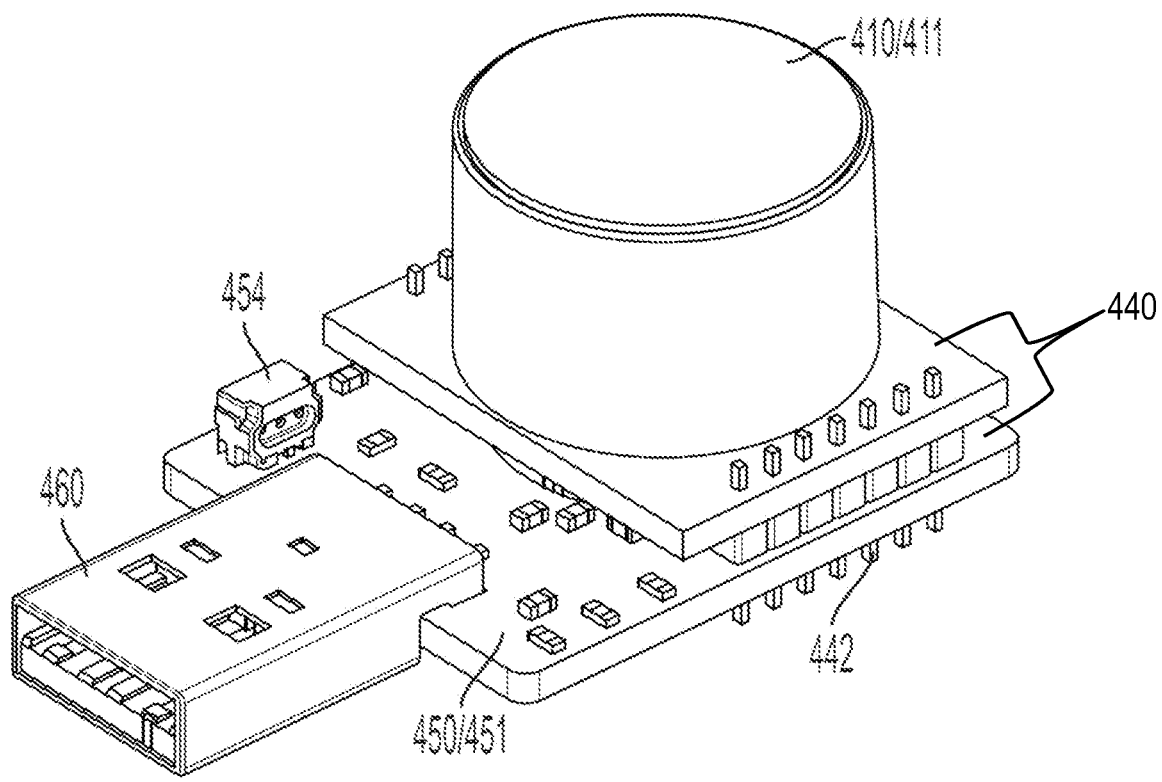
FIG. 5A is an illustration of the interior of a sensor module in accordance with one or more embodiments of the present disclosure.
Figure 5B:
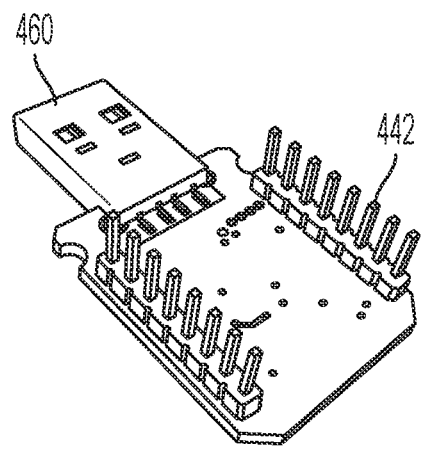
FIG. 5B is an illustration of the interior of the sensor module of FIG. 5A with a first circuit board removed to reveal a second circuit board.
Figure 5C:
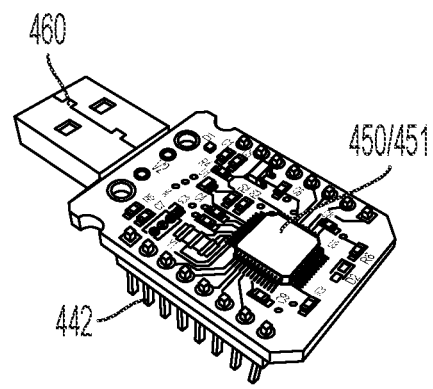
FIG. 5C is an illustration of the reverse of FIG. 5B

With reference to FIGS. 1B and 2B, the housing 100 includes one or more manifolds 110 to direct air flow from the atmosphere surrounding the housing 100 to the at least one modular gas sensor 400. In one or more embodiments, the manifolds 110 comprise flow channels 112 connecting a sampling port 114 provided in the housing 100 with each of the individual modular gas sensors 400 and ancillary sensor modules 401 which are configured to measure presence or concentrations of species within the surrounding atmosphere. For example, an ancillary sensor module 401 configured to measure the presence and/or concentration of moisture in the surrounding atmosphere may be fluidly connected to one or more of the manifolds 110. The manifolds 110 provide routing for the necessary sampling of the atmosphere surrounding the health exposure sensor system 10 to ensure delivery of atmospheric samples to each of the individual modular gas sensors 400 and ancillary sensor modules 401 as appropriate. It will be appreciated that in various embodiments, the flow channels 112 connecting the sampling port 114 provided in the housing 100 with each of the individual modular gas sensors 400 and ancillary sensor modules 401 may be provided as dedicated flow channels or as serial flow channels. Specifically, a dedicated flow channel represents a flow channel 112 which provides a direct route between the sampling port 114 and the individual modular gas sensor 400 or ancillary sensor module 401. Conversely, a serial flow channel represents a flow channel 112 which provides flow to multiple individual modular gas sensors 400 and/or ancillary sensor modules 401 in a sequential manner. In one or more embodiments, the manifold 110 terminates in an exhaust port 115 to allow venting of air from the manifold 110 and follow channels 112.

In one or more embodiments, the manifolds 110 include a sealing gasket 116 to form a substantially air-tight connection with each of the individual modular gas sensors 400 and ancillary sensor modules 401. It will be appreciated that a substantially air-tight connection between the manifolds 110 and each of the individual modular gas sensors 400 and ancillary sensor modules 401 is desirable to ensure sufficient flow of sampled air into each of the individual modular gas sensors 400 and ancillary sensor modules 401 as well as to limit passage of particulates or other debris into an interior space of the housing 100. In one or more embodiments the sealing gasket 116 may be formed from a supple material as known to those skilled in the art such as neoprene, closed cell foam, rubber, or leather. It will be appreciated that the material forming the sealing gasket 116 should be selected to resist degradation with exposure to heat, moisture, chemical vapors, or other species anticipated to be encountered in normal operations. In further embodiments, the sealing gasket 116 may be formed from a rigid material or a semi-rigid material and comprise a geometry to mate and interface with an air inlet or opening 430 on the individual modular gas sensors 400 and ancillary sensor modules 401.

In one or more embodiments, the manifold 110 includes flow baffles 118 to control the volume of airflow to one or more of the individual modular gas sensors 400 and/or ancillary sensor modules 401. The flow baffles 118 allow for a particular individual modular gas sensor 400 and/or ancillary sensor module 401 to be isolated and protected from airflow during inoperative periods to prevent fouling of the individual modular gas sensor 400 or ancillary sensor module 401. Further, the flow baffles 118 may allow for greater airflow to be provided to certain individual modular gas sensors 400 and/or ancillary sensor modules 401 than other individual modular gas sensors 400 and/or ancillary sensor modules 401 based on the operating specifications of each sensor unit 400/401. In various embodiments, control of the flow baffles 118 may be completed on a real-time basis by the microprocessor 220 or may be manually configured during set-up and installation of the individual modular gas sensors 400 and ancillary sensor modules 401.

In one or more embodiments, the housing 100 includes an air intake filter 140 disposed in a flow path of the one or more manifolds 110. It will be appreciated that the air intake filter 140 may filter out one or more species from the atmospheric air being drawn into the health exposure sensor system 10. In one or more embodiments, the air intake filter 118 is configured to remove particulate matter from the sampled air to reduce or eliminate fouling of the individual modular gas sensors 400 and ancillary sensor modules 401. In one more embodiments, the air intake filter 140 is configured to remove one or more chemical species from the sampled air to reduce or eliminate species which may interfere with operation of or damage the individual modular gas sensors 400 or ancillary sensor modules 401. The air intake filter 140, in various embodiments, may be provided at or proximal the sampling port 114 of the housing 100, at or proximal one or more of the individual modular gas sensors 400 or ancillary sensor modules 401, or within any of the flow channels 112 of the manifolds 110.

In one or more embodiments, the health exposure sensor system 10 includes an air intake system 600. The air intake system 600 may include an air pump 610 configured to propel the atmosphere surrounding the housing 100 to the individual modular gas sensors 400 and ancillary sensor modules 401 through the one or more manifolds 110. The air pump 610 allows for the atmosphere surrounding the housing 100 to be driven to the individual modular gas sensors 400 and ancillary sensor modules 401 through the one or more manifolds 110 thereby providing greater flow than would be present with natural diffusion through the manifolds 110. In various embodiments, the air pump 610 provides a flow to each applicable individual modular gas sensor 400 and ancillary sensor module 401 of 0.3 liters per minute (LPM) to 0.8 LPM. It will be appreciated that as the health exposure sensor system 10 may include multiple individual modular gas sensors 400 and/or ancillary sensor modules 401.

In one or more embodiments and with reference to FIGS. 1A and 1B, the housing 100 includes access ports 150 on one or more exterior walls of the housing. The access ports 150 are individually aligned with one of the array of data ports 230 provided on the monitoring platform 200 allowing for the individual modular gas sensors 400 and ancillary sensor modules 401 to be inserted into the housing 100 and connect with the data ports 230 without necessitating opening or disassembly of the housing 100. Further, the access ports 150 may be configured to actively engage the individual modular gas sensors 400 and ancillary sensor modules 401 upon insertion into the housing 100. For example, the housing 100 proximal the access port 150 may comprise a geometry to apply a friction fit with the individual modular gas sensors 400 and ancillary sensor modules 401, comprise a spring-loaded or otherwise releasable engagement pin to interface with a complementary depression on the individual modular gas sensors 400 and ancillary sensor modules 401, or comprise a movable member able to be positioned to restrain removal of the individual modular gas sensors 400 and ancillary sensor modules 401. It will further be appreciated that in one or more embodiments, engagement of the individual modular gas sensors 400 and ancillary sensor modules 401 with the data ports 230 may suffice to retain the individual modular gas sensors 400 and ancillary sensor modules 401 within the housing 100 with the connection at the data port 230 providing sufficient retentive force.

In one or more embodiments, the power source 300 affixed to the housing 100 is utilized for the energy needs of the health exposure sensor system 10. For example, the power source 300 may provide operational power to the circuit board 210 and the various components connected to the circuit board 210. Specifically, the power source 300 may power the microcontroller 220. Additionally, in one or more embodiments, the power source 300 may additionally power various peripherals attached to the array of data ports 230 provided on the circuit board 210 including the modular gas sensors 400 and/or the ancillary sensor modules 401. In various embodiments, the power source 300 may be a battery having a capacity of 1000 to 7000 milliamp-hours (mAh), 1400 mAh to 5000 mAh, or 1800 mAh to 3500 mAh. In various embodiments, the power source 300 may be a 3.7 volt battery, a 1.5 volt battery, a 3 volt battery, or a 9 volt battery. For example, a 18650 lithium ion rechargeable battery may be utilized as the bower source 300.

It will further be appreciated that in one or more embodiments, the modular gas sensors 400 and/or the ancillary sensor modules 401 may additionally or alternatively include a separate battery to power each individual modular gas sensor 400 and/or ancillary sensor module 401 independent of the power source 300. Such arrangement allows for the modular gas sensors 400 and/or the ancillary sensor modules 401 to maintain a powered state disconnected from the monitoring platform 200 and external computing device 900. Additionally, provision of a separate battery within one of more of the modular gas sensors 400 and/or the ancillary sensor modules 401 to power such individual modular gas sensor 400 and/or ancillary sensor module 401 independent of the power source 300 allows for a specific modular gas sensor 400 and/or the ancillary sensor module 401 to operate at a different voltage or other electrical parameter than the remaining units without requiring additional units and complexity for manipulation of the electrical output of the power source 300.

It will be appreciated that the air pump 610 provided as a component of the air intake system 600 must have power for operation. In one or more embodiments, the air pump 610 may be powered with a battery power source disposed within or affixed to the housing 100. Such battery power source may be the power source 300 or may be an additional auxiliary power source. It will be appreciated that operation of the air pump 610 on a separate circuit and with electrical energy separate from that of the power source 300 reduces power demands on the power source 300.

In one or more embodiments, the health exposure system 10 further includes an external power port 310 configured for connection to an electrical power supply separate from the health exposure system 10 to allow for recharging or augmentation of the power source 300 and/or the auxiliary power source provided as a component of the air intake system 600. In various embodiments, the external power port 310 may comprise a standard interface, such as USB, 4-pin connectors, or single prong.

The health exposure system 10 may also include one or more data storage modules 700. In one or more embodiments, the data storage module 700 is affixed to the circuit board 210 and is configured to retain outputs from multiple modular gas sensors 400 and/or ancillary sensor modules 401 and/or particulate sensor modules 402. In one or more embodiments, the one or more data storage modules 700 are integrated with the modular gas sensors 400 and/or ancillary sensor modules 401 and/or particulate sensor module 402. In one or more embodiments, the data storage module 700 is provided as permanent memory integrated with the circuit board 210, the individual modular gas sensors 400, the individual ancillary sensor modules 401, and/or the individual particulate sensor modules 402. In one or more embodiments, the data storage module 700 may additionally or alternatively be provided as removable memory such as a non-volatile memory card (commercially available as an SD card from numerous manufacturers) disposed within the circuit board 210, the individual modular gas sensors 400, the individual ancillary sensor modules 401 and/or the individual particulate sensor modules 402. It will be appreciated that provision of removable memory allows for adjustment of memory capacity within the health exposure system 10, and more particularly the individual modular gas sensors 400 and/or the individual ancillary sensor modules 401, to accommodate anticipated data storage needs for differing combinations of modular gas sensors 400 and/or ancillary sensor modules 401 and/or particulate sensor modules 402 and differing service durations between data downloads.

In one or more embodiments, the health sensor system 10 includes a wireless data transmitter 800. The wireless data transmitter 800 may be configured to allow wireless transmission of data stored in the one or more data storage modules 700 using a known wireless data transfer protocol. Non-limiting examples of wireless data transfer protocols include Bluetooth and Wi-Fi (IEEE 802.11).

Figure 7:
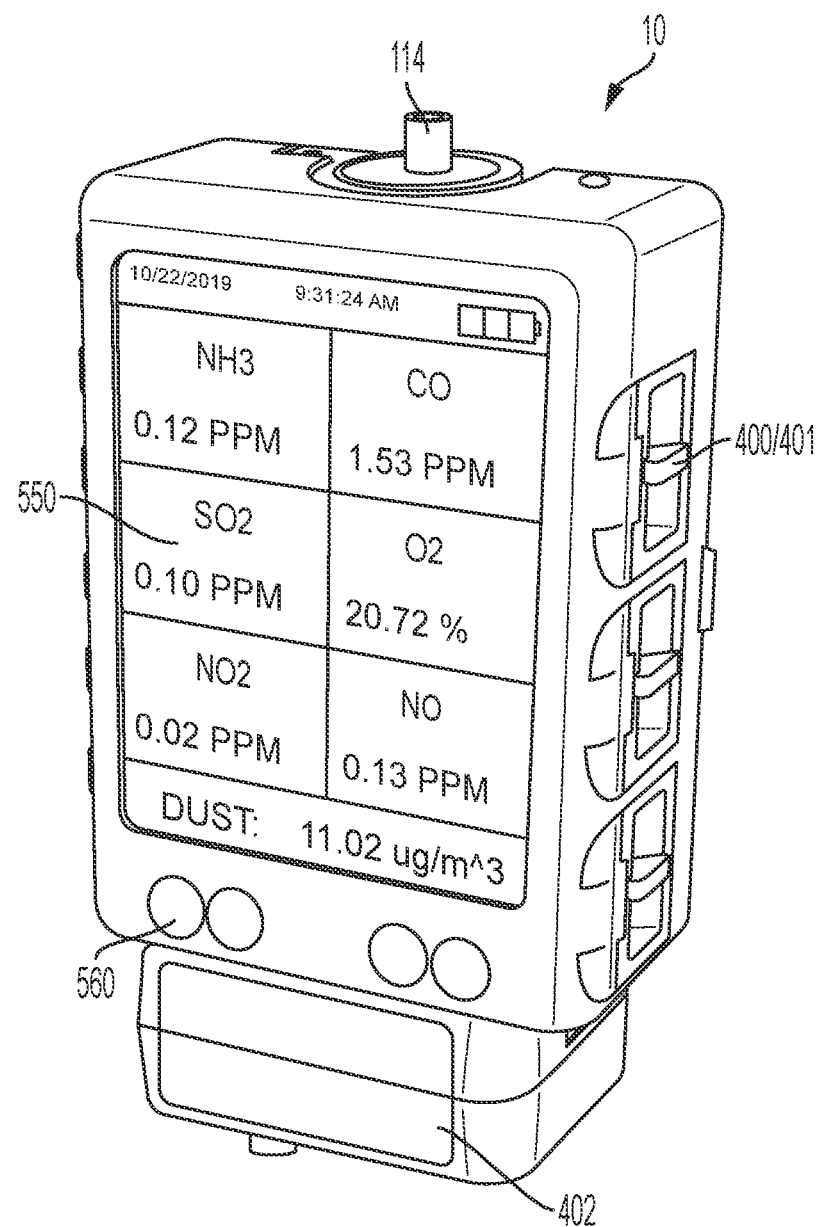
FIG. 7 is an illustration of a health exposure sensor system with display on a graphical user interface and attachment of a particle sensor module in accordance with one or more embodiments of the present disclosure.

In one or more embodiments and with reference to FIGS. 1A and 7, the health exposure sensor system 10 further comprises a graphical user interface (GUI) 550 affixed to or integral with the housing 100 for user interaction with the microprocessor 220, the modular gas sensors 400, and/or the ancillary sensor modules 401. Integration or direct fixation to the housing 100 of the GUI 550 ensures that ready access to the GUI 550 is always present and without the need for auxiliary equipment or dependence of the battery life or connectivity status of such auxiliary equipment. The GUI 550 may be a touch screen or an LED/LCD display. Further, the GUI 550 may connect to the circuit board 210 via a display connector 552. It will be appreciated that the display connector 552 provides an interface between the microcontroller 220 and the GUI 550. Further, the health exposure sensor system 10 may further include one or more input buttons 560 to allow for user interaction with the GUI 550. It will be appreciated that when the GUI 550 comprises a touch screen display, the input buttons 560 may be omitted with full interaction via the touch screen or remain to allow for input independent of the touch screen for functionality such as "enter" or "power" to conform an input or initialize the system 10.

In one or more embodiments, the health exposure sensor system 10 utilizes the functionality of the wireless data transmitter 800 to interact with a mobile computing device 900 and leverage a graphical user interface (GUI) 550 provided as part of the mobile computing device 900 for user interaction with the microprocessor 220, the modular gas sensors 400, and/or the ancillary sensor modules 401. For example, the health exposure system 10 may communicate with a cellular phone such that the integrated screen of the cellular phone may be leverage to provide a user-friendly display of operating parameters associated with the health exposure sensor system 10. Provision of the GUI 550 as a separate unit integrated in a mobile computing device 900, such as illustrated in FIG. 6, allows for the power requirements of such GUI 550 to not detrimentally effect the power reserves of the health exposure sensor system 10.

The GUI 550, whether provided in a mobile computing device 900, as in FIG. 6, or provided as part of the housing 100, as in FIG. 7, allows for an operator to access the microcontroller 220 and/or individual sensor units 400/401 within the health exposure sensor system 10 in a user-friendly manner. Specifically, in various embodiments, the GUI 550 may display real-time or trending values from one or more of the sensor units 400/401, provide an interface for calibration procedures of individual system components, provide informational or emergency alerts, or combinations thereof.

In one or more embodiments, the GUI 550 may allow a user to perform calibration and/or other maintenance and status checks on the various modular gas sensors 400 and/or ancillary sensor modules 401. For example, the GUI 550 may allow the user to check the remaining power reserves in the power source 300, the time-in-service, or other operational parameters for each of the various modular gas sensors 400 and/or ancillary sensor modules 401 without disconnection and removal from the health exposure sensor system 10. On board calibration using the GUI 550 as an intuitive interface for the user similarly allows calibration to be completed or updated on an as needed basis without removal of the various modular gas sensors 400 and/or ancillary sensor modules 401 from the health exposure sensor system 10.

In one or more embodiments, the microcontroller 220 may be configured to perform an automatic calibration of various modular gas sensors 400 and/or ancillary sensor modules 401 upon connection to the data port 230 based on specific calibration procedures in accordance with the type of modular gas sensor 400 or ancillary sensor module 401. Automatic calibration ensures that the various modular gas sensors 400 and/or ancillary sensor modules 401 provide accurate observations before placing the health exposure sensor system 10 into service. In one or more embodiments, automatic calibration entails provision of a known amount of input gas of interest (or other known parameter) to begin the calibration process and adjust the sensitivity of the various modular gas sensors 400 and/or ancillary sensor modules 401 to align to the known input gas concentration or other parameter.

In operation, the health exposure sensor system 10 and more particularly the interface with the multiple modular gas sensors 400 and/or ancillary sensor modules 401 may function in accordance with multiple communication protocols allowing for switching between such communication protocols on demand. In one or more embodiments, the gas sensor microcontroller 450 includes at least one on-chip universal asynchronous receiver-transmitter (UART) peripheral 452 and at least one on-chip USB peripheral 454 with both the UART peripheral 452 and the USB peripheral 454 having input/output (I/O) functionality and connection to the data port interface 460 of the modular gas sensor 400 for communication external to the modular gas sensor 400. Similarly, in one or more embodiments, the ancillary sensor 401 may include the ancillary sensor microcontroller 451 with at least one on-chip universal asynchronous receiver-transmitter (UART) peripheral 452 and at least one on-chip USB peripheral 454 with both the UART peripheral 442 and the USB peripheral 454 having input/output (I/O) functionality and connection to the data port interface 460 of the ancillary sensor 401 for communication external to the ancillary sensor module 401. It will be appreciated that the UART peripheral 452 and the USB peripheral 454 are on-chip peripherals meaning that are included inside the actual microcontroller chip (gas sensor microcontroller 450 and/or ancillary sensor microcontroller 451) of the modular sensor 400/401 itself.

On-chip placement of the peripherals in part makes the gas sensor microcontroller 450 and/or ancillary sensor microcontroller 451 be microcontrollers instead of being microprocessors.

It is generally appreciated that a microcontroller is more integrated than a microprocessor. Specifically, a microprocessor provides computational functions, but typically requires external components to provide memory, USB interfaces, and other such functionality. Conversely, a microcontroller combines the functionality of all these components and more into a single chip.

Operation of the health exposure sensor system 10 with multiple communication protocols allows the health exposure system 10 to operate with reduced power consumption and thereby for a longer period of time with a single charge of the power source 300. Specifically, such arrangment enables the currently disclosed sensor units 400/401 of the health exposure sensor system 10 to function as a low power standalone device using UART protocols while deployed in the health exposure sensor system 10 as well as interface with higher power systems using USB protocols when connected to a computing device 900, for example. It will be appreciated that USB protocol requires a higher power requirement (generall in excess of 148 mW) which is not desirable for battery life, even though USB devices are widely available in the electronics industry. Conversely, the universal asynchronous receiver-transmitter (UART) communication proctol typically operates under lower power requirement (generally less than 10 mW) which naturally extends battery life and operational paradigms for the health exposure sensor system 10.

To take advantage of the low power requirement of UART connection and the wide acceptance of USB connection in the industry, the health exposure snesor system 10, in one or more embodiments, incorporates sensors 400/401 which are capable of dynamically switching between a universal asynchronous receiver-transmitter (UART) and USB physical layers (as defined under the Open Systems Interconnection (OSI) Model) within the sensor microcontroller chip. Typically, a given physical interface on a device supports only a single physical layer and peripheral in contrast to the current system where a single physical interface in the modular gas sensor 400 and/or ancillary sensor module 401 supports both USB and UART peripherals 452/454 with dynamic switching therebetween for communication using a single data port 230 and data port interface 460. Switching between several interface peripherals at a single port via multiplexing is possible, but typically requires the use of additional electronic component, such as a multiplexer. Such additional components adds weight and volume to the device and is not desirable for a compact wearable system. As such, embodiments of the present disclosure achieve dynamic switching between multiple interface peripherals at a single port without implementation of a multiplexer.

In accordance with one or more embodiments, dynamic switching between the UART and USB on-chip peripherals 452/454 at the data ports 230 of the monitoring platform 200 and data port interface 460 of the modular gas sensor 400 and/or the ancillary sensor module 401 is accomplished by putting both on-chip peripherals such as USB 454 and UART 452 on the sensor microcontroller 450/451 and connecting the peripherals 452/454 to a single data port interface 460 via the gas sensor circuit board 440 in the modular gas sensor 400 and/or the ancillary sensing unit circuit board 441 in the ancillary sensor module 401. Then each of the on-chip peripherals 452/454 may be selectively enabled individually and one at a time via the digital input and output (I/O) configuration of the gas sensor microcontroller 450 or ancillary sensor microcontroller 451. Such device control mechanism reduces the power requirements, and thus extends the duration of operation between recharging of the power source 300 and/or auxiliary power source, for the modular gas sensor 400 and/or the ancillary sensor module 401. This is achieved by using UART communication via the UART peripheral 452 as much as possible and using USB protocol via the USB peripheral 454 only as necessary. In addition, such design also reduces the number of parts required to take advantage of the features of both UART and USB communication protocols as the need for a multiplexer is avoided.

Figure 8:
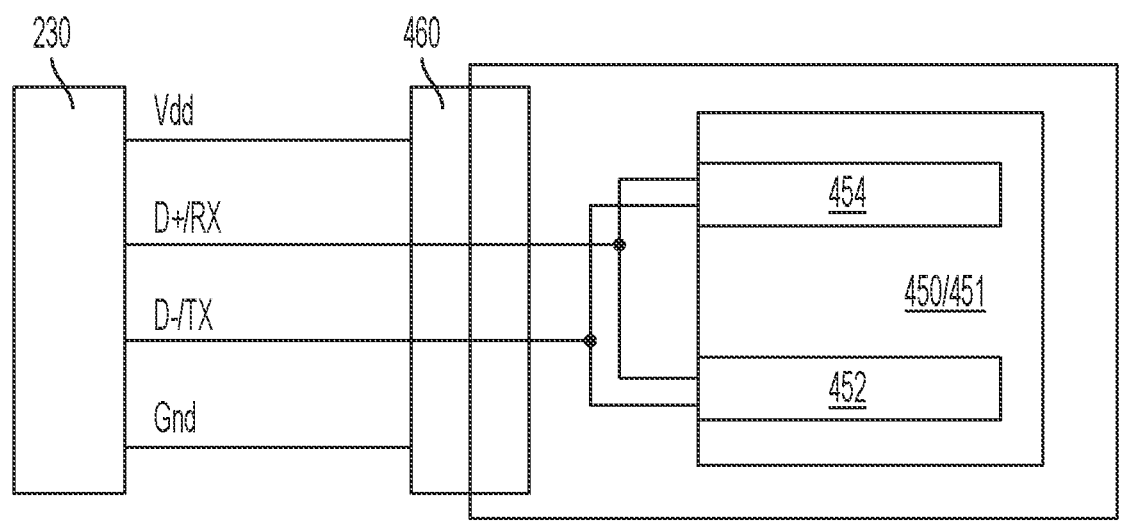
FIG. 8 is a block diagram of dynamic switching between physical layers in the data port and data port interface of a health exposure sensor system in accordance with one or more embodiments of the present disclosure.

With reference to FIG. 8, an example embodiment with dynamic switching between the on-chip peripherals 452/454 of the sensor microcontroller 450/451 at the data port 230 and data port interface 460 is illustrated. The microcontroller in the sensor module 400/401, for example the gas sensor microcontroller 450 or the ancillary sensor microcontroller 451, include a USB controller and a UART controller integrated therein serving as the on-chip peripherals 452/454. It will be understood that the USB controller is configured to operatively communicate in accordance with standard USB protocols. Similarly, the UART controller is configured to operatively communicate win accordance with UART protocols. Both the USB controller and the UART controller are communicatively connect with the data port interface 460 of the modular gas sensor 400 or ancillary sensor module 401. One skilled in the art will appreciate that USB communication protocols include a ground connection (Gnd), a supply voltage connection (Vdd), a positive data terminal connection (D+), and a negative data terminal connection (D−). Similarly, UART communication protocols include a ground connection (Gnd), a supply voltage connection (Vdd), a transmission connection (TX), and a data reception connection (RX). The data port 230 provided on the monitoring platform 200 then has the same connection scheme allowing for communication between the gas sensor microcontroller 450 or ancillary sensor microcontroller 451 and the microcontroller 220 on the monitoring platform circuit board 210 via the data port 230 and the data port interface 460. In operation only D+/D− or TX/RX are active as controlled by internal configuration registers in the gas sensor microcontroller 450 or ancillary sensor microcontroller 451 which exclusively enable communication through USB protocol or UART protocol by activating only one of the USB controller and the UART controller at a given time.

In one or more embodiments, the UART peripheral 452 is enabled for communication internally within the health exposure sensor system 10. Utilizing the UART peripheral 452 for communication internally within the health exposure sensor system 10 allows for low power operation of the health exposure sensor system 10 and extended battery life, such as in circumstances when the sensor system is being worn by a user in the field without a connection to utility power supply. Including UART communication protocols in each component of the health exposure sensor system 10 allows the system 10 to complete internal communication and control using the low-power UART communication peripheral 452 and protocols.

In one or more embodiments, the USB peripheral 454 is enabled for communication with a USB device external to the health exposure sensor system 10. The USB peripheral 454 may also be utilized for communication internally within the health exposure sensor system 10. It will be appreciated that many computing devices 900 such as mobile phones, laptops, and tablet PCs include USB ports and are configured to communicate using USB protocols. As such, it is advantageous for the sensor modules 400/401 within the health exposure sensor system 10 to also be configured to communication using USB protocols. When the sensor modules, such as the modular gas sensor 400 or ancillary sensor module 401, of the health exposure sensor system 10 are removed from the data ports 230 and connected to a USB enabled device or a USB enabled device is connected to a data port 230, the USB peripheral 454 may be activated to allow for communication. Upon activation of the USB peripheral 454, the UART peripheral 452 is deactivated and all communication is completed using USB protocols. While the USB communication protocols are more energy intense, it is beneficial to have the ability to switch from UART communication to USB communication to allow for operation and connection of the modular gas sensor 400 or ancillary sensor module 401 to USB enabled devices external to the health exposure sensor system 10.

Throughout the present disclosure there is reference to various microcontrollers including at least the microcontroller 220, the gas sensor microcontrollers 450, and the ancillary sensor microcontrollers 451. Each of these microcontrollers represent compact integrated circuits designed to govern the specific operation of the system or device of which they are integrated. For example, the microcontroller 220 govern the specific operation of the health exposure sensor system 10 overall and more particularly the operations of the monitoring platform 200, the gas sensor microcontrollers 450 govern the specific operation of the modular gas sensors 400, and the ancillary sensor microcontrollers 451 govern the specific operation of the ancillary sensor modules 401. One skilled in the art has familiarity with microcontrollers in general and is capable of selection of an appropriate microcontroller for governing the specific operational guidelines of the microcontroller 220, the gas sensor microcontrollers 450, and the ancillary sensor microcontrollers 451. Examples of suitable microcontrollers include MSP430FR5994IPMR (Texas Instruments, Texas), CC1352 (Texas Instruments, Texas), PIC32MK1024GPE100 (Microchip Technology, Arizona).

It will be appreciated that the health exposure sensor system 10 is sized and configured to be unobtrusively worn on the person or apparel of a user in one or more embodiments. For purposes of the present disclosure, unobtrusively means that the dimensions of the health exposure sensor system 10 do not constitute an obstruction to performance of the normal physical movements of the wearer. In one or more embodiments, the health exposure sensor system 10 may be sized and configured to fit within a pocket or pouch provided on an article of clothing. For example, the health exposure sensor system 10 may be operationally disposed in a pouch on an article of Modular Lightweight Load-carrying Equipment (MOLLE) or body armor of a soldier as well as the vest or tool belt of a blue-collar worker.

Having described various embodiments, it should be understood that the various aspects of the health exposure sensor system are described and such aspects may be utilized in conjunction with various other aspects.

In a first aspect, the disclosure provides a health exposure sensor system. The system comprises a housing, a monitoring platform disposed in the housing, and a power source. The monitoring platform comprises at least one modular gas sensor, a circuit board comprising a microcontroller, and an array of data ports for connecting the at least one modular gas sensor to the circuit board. The housing comprises one or more manifolds to direct air flow from the atmosphere surrounding the housing to the at least one modular gas sensor. The modular gas sensor comprises a gas detector enclosed in a sensor housing with an opening for gas diffusion to the gas detector and a gas sensor circuit board comprising a gas sensor microcontroller. The gas sensor microcontroller comprises at least one on-chip universal asynchronous receiver-transmitter (UART) peripheral and at least one on-chip USB peripheral, wherein both the UART peripheral and the USB peripheral comprise input/output (I/O) functionality and are connected to both the gas sensor microcontroller and a single data port interface for communication external to the modular gas sensor.

In a second aspect, the disclosure provides the system of the first aspect, in which the housing comprises a base configured for securement of the monitoring platform and a lid configured to mate with the base.

In a third aspect, the disclosure provides the system of the first or second aspect, in which the housing further comprises an air intake filter disposed in a flow path of the one or more manifolds.

In a fourth aspect, the disclosure provides the system of any of the first through third aspects, in which the health exposure sensor system further comprises an air intake system, the air intake system comprising an air pump configured to propel the atmosphere surrounding the housing to the at least one modular gas sensor through the one or more manifolds.

In a fifth aspect, the disclosure provides the system of the fourth aspect, in which the air pump is powered with a battery power source disposed within or affixed to the housing.

In a sixth aspect, the disclosure provides the system of any of the first through fifth aspects, in which the data port and the data port interface comprise USB type connectors allowing the modular gas sensor and the data ports to communicatively connect.

In a seventh aspect, the disclosure provides the system of the method of any of the first through sixth aspects, in which the UART peripheral and the USB peripheral may be selectively enabled individually via digital I/O configuration of the microcontroller provided with the circuit board of the monitoring platform.

In an eighth aspect, the disclosure provides the system of any of the first through seventh aspects, in which the modular gas sensor is operable to be removed from the data port of the monitoring platform and connected to a USB port of a computing device, the computing device powering the modular gas sensor via the connection to the USB port and accessing a real-time readout of measurements by the modular gas sensor.

In a ninth aspect, the disclosure provides the system of any of the first through eighth aspects, in which the modular gas sensor outputs a modulated current or voltage signal indicative of the presence of an air quality contaminant in the atmosphere surrounding the housing.

In a tenth aspect, the disclosure provides the system of any of the first through ninth aspects, in which the health exposure sensor system further comprises one or more ancillary sensor modules communicatively connected with the monitoring platform, the ancillary sensor modules configured to monitor atmospheric parameters beyond those monitored by the at least one modular gas sensor.

In an eleventh aspect, the disclosure provides the system of the tenth aspect, in which the one or more ancillary sensor modules are selected to monitor one or more of sound intensity, radiation, temperature, pressure, and humidity.

In a twelfth aspect, the disclosure provides the system of the tenth or eleventh aspect, in which the one or more ancillary sensor modules interface with the circuit board via one or more of the data ports.

In a thirteenth aspect, the disclosure provides the system of any of the first through twelfth aspects, in which the health exposure sensor system further comprises a graphical user interface (GUI) affixed to or integral with the housing for user interaction with the microprocessor and/or the modular gas sensor.

In a fourteenth aspect, the disclosure provides the system of any of the first through thirteenth aspects, in which the health exposure system further comprises a wireless data transmitter configured to interact with a mobile computing unit providing a graphical user interface (GUI) for user interaction with the microprocessor and/or the modular gas sensor.

In a fifteenth aspect, the disclosure provides the system of any of the first through fourteenth aspects, in which the health exposure system further comprises one or more atmospheric sensors connected to the circuit board for monitoring one or more of temperature, pressure, and humidity of the atmosphere surrounding the housing.

In a sixteenth aspect, the disclosure provides the system of any of the first through fifteenth aspects, in which the health exposure sensor system further comprises a particulate sensor module communicatively connected with the monitoring platform, the particulate sensor module configured to monitor particulates in the atmosphere surrounding the health exposure sensor system.

In a seventeenth aspect, the disclosure provides the system of any of the first through sixteenth aspects, in which the health exposure system further comprises one or more data storage modules.

In an eighteenth aspect, the disclosure provides the system of the seventeenth aspect, in which the data storage module is affixed to the circuit board and is configured to retain outputs from multiple modular gas sensors, particulate sensor modules, and/or atmospheric sensors.

In a nineteenth aspect, the disclosure provides the system of the seventeenth aspect, in which the one or more data storage modules are integrated with the modular gas sensors, particulate sensor modules, and/or atmospheric sensors.

In a twentieth aspect, the disclosure provides the system of any of the first through nineteenth aspects, in which the health exposure system further comprises a global positioning system (GPS) configured to correlate data received from the modular gas sensors and/or ancillary sensor modules with location of sampling.

In a twenty-first aspect, the disclosure provides the system of any of the first through twentieth aspects, in which the health exposure system further comprises an external power port configured for connection to a power source separate from the health exposure system to allow for recharging or augmentation of the power source provided as a component of health exposure monitoring system.

In a twenty-second aspect, the disclosure provides the system of any of the first through twenty-first aspects, in which the microcontroller is configured to perform an automatic calibration of the modular gas sensor upon connection to the data port based on specific calibration procedures in accordance with the modular gas sensor type.

In a twenty-third aspect, the disclosure provides the system of any of the first through twenty-second aspects, in which the system is sized and configured to be unobtrusively worn on the person or apparel of a user.

In a twenty-fourth aspect, the disclosure provides method of operating a health exposure sensor system, the health exposure sensor system according to any of the first through twenty-third aspects. The method comprises selectively enabling individually via digital I/O configuration of the microcontroller either the UART peripheral or the USB peripheral.

In a twenty-fifth aspect, the disclosure provides method of operating a health exposure sensor system. The health exposure sensor system comprises a monitoring platform which comprises at least one modular gas sensor, a circuit board comprising a microcontroller, and an array of data ports for connecting the at least one modular gas sensor to the circuit board. The modular gas sensor comprises a gas detector enclosed in a sensor housing with an opening for gas diffusion to the gas detector and a gas sensor circuit board comprising a gas sensor microcontroller. The gas sensor circuit board comprises at least one on-chip universal asynchronous receiver-transmitter (UART) peripheral and at least one on-chip USB peripheral, wherein both the UART peripheral and the USB peripheral comprise input/output (I/O) functionality and are connected to a single data port interface for communication external to the modular gas sensor. The method comprises selectively enabling individually either the UART peripheral or the USB peripheral via digital I/O configuration of the gas sensor microcontroller.

In a twenty-sixth aspect, the disclosure provides the method of the twenty-fourth or twenty-fifth aspect, in which the UART peripheral is enabled for communication internally within the health exposure sensor system.

In a twenty-seventh aspect, the disclosure provides the method of the twenty-fourth or twenty-fifth aspect, in which the USB peripheral is enabled for communication with a USB device external to the health exposure sensor system.

In a twenty-eighth aspect, the disclosure provides the method of the twenty-fourth or twenty-fifth aspect, in which the USB peripheral is enabled for communication with a USB device external to the health exposure sensor system as well as communication internally within the health exposure sensor system.

It should be apparent to those skilled in the art that various modifications and variations may be made to the embodiments described within without departing from the spirit and scope of the claimed subject matter. Thus, it is intended that the specification cover the modifications and variations of the various embodiments described within provided such modification and variations come within the scope of the appended claims and their equivalents.

As used throughout, the singular forms "a," "an" and "the" include plural referents unless the context clearly dictates otherwise. Thus, for example, reference to "a" component includes aspects having two or more such components, unless the context clearly indicates otherwise.

Optional or optionally means that the subsequently described event or circumstances may or may not occur. The description includes instances where the event or circumstance occurs and instances where it does not occur.

It should be understood that any two quantitative values assigned to a property or measurement may constitute a range of that property or measurement, and all combinations of ranges formed from all stated quantitative values of a given property or measurement are contemplated in this disclosure.

As used here and in the appended claims, the words "comprise," "has," and "include" and all grammatical variations thereof are each intended to have an open, non-limiting meaning that does not exclude additional elements or steps.

Having described the subject matter of the present disclosure in detail and by reference to specific embodiments thereof, it is noted that the various details disclosed within should not be taken to imply that these details relate to elements that are essential components of the various embodiments described within, even in cases where a particular element is illustrated in each of the drawings that accompany the present description. Further, it should be apparent that modifications and variations are possible without departing from the scope of the present disclosure, including, but not limited to, embodiments defined in the appended claims. More specifically, although some aspects of the present disclosure are identified as particularly advantageous, it is contemplated that the present disclosure is not necessarily limited to these aspects.

What is claimed is:

1. A health exposure sensor system, the system comprising: a housing, a monitoring platform disposed in the housing, and
a power source;
wherein:
the monitoring platform comprises at least one modular gas sensor, a circuit board comprising a main microcontroller, and an array of data ports for connecting the at least one modular gas sensor to the circuit board; and
the housing comprises one or more manifolds to direct air flow from the atmosphere surrounding the housing to the at least one modular gas sensor;
wherein each modular gas sensor comprises:
a gas detector enclosed in a sensor housing with an opening for gas diffusion to the gas detector; and
a gas sensor circuit board comprising a gas sensor microcontroller, wherein the gas sensor microcontroller comprises at least one on-chip universal asynchronous receiver-transmitter (UART) peripheral and at least one on-chip USB peripheral, wherein both each UART peripheral and each USB peripheral comprise input/output (I/O) functionality and are connected to a single data port interface for communication external to the at least one modular gas sensor.

2. The health exposure sensor system of claim 1, wherein the housing comprises a base configured for securement of the monitoring platform and a lid configured to mate with the base.

3. The health exposure sensor system of claim 1, wherein the housing further comprises an air intake filter disposed in a flow path of the one or more manifolds.

4. The health exposure sensor system of claim 1, wherein the health exposure sensor system further comprises an air intake system, the air intake system comprising an air pump configured to propel the atmosphere surrounding the housing to the at least one modular gas sensor through the one or more manifolds.

5. The health exposure sensor system of claim 1, wherein each data port and each data port interface comprise USB type connectors allowing each modular gas sensor and the data ports to communicatively connect.

6. The health exposure sensor system of claim 1, wherein each UART peripheral and each USB peripheral may be selectively enabled individually.

7. The health exposure sensor system of claim 1, wherein each modular gas sensor is operable to be removed from each data port of the monitoring platform and connected to a USB port of a computing device, the computing device powering each modular gas sensor via the connection to each USB port and accessing a real-time readout of measurements by each modular gas sensor.

8. The health exposure sensor system of claim 1, wherein the health exposure sensor system further comprises one or more ancillary sensor modules communicatively connected with the monitoring platform, each ancillary sensor modules configured to monitor atmospheric parameters beyond those monitored by the at least one modular gas sensor.

9. The health exposure system of claim 8, wherein the one or more ancillary sensor modules are selected to monitor one or more of sound intensity, radiation, temperature, pressure, and humidity.

10. The health exposure sensor system of claim 8, wherein the one or more ancillary sensor modules interface with the circuit board via one or more of the data ports.

11. The health exposure sensor system of claim 1, wherein the health exposure sensor system further comprises a graphical user interface (GUI) affixed to or integral with the housing for user interaction with the microprocessor and/or each modular gas sensor.

12. The health exposure sensor system of claim 1, wherein the health exposure sensor system further comprises a wireless data transmitter configured to interact with a mobile computing unit providing a graphical user interface (GUI) for user interaction with the microprocessor and/or each modular gas sensor.

13. The health exposure sensor system of claim 1, wherein the health exposure sensor system further comprises one or more atmospheric sensors connected to the circuit board for monitoring one or more of temperature, pressure, and humidity of the atmosphere surrounding the housing.

14. The health exposure sensor system of claim 1, wherein the health exposure sensor system further comprises a particulate sensor module communicatively connected with the monitoring platform, the particulate sensor module configured to monitor particulates in the atmosphere surrounding the health exposure sensor system.

15. The health exposure sensor system of claim 1, wherein the health exposure sensor system further comprises one or more data storage modules.

16. The health exposure sensor system of claim 1, wherein the health exposure sensor system further comprises a global positioning system (GPS) configured to correlate data received from each modular gas sensors and/or each ancillary sensor modules with location of sampling.

17. The health exposure sensor system of claim 1, wherein the health exposure sensor system further comprises an external power port configured for connection to a power source separate from the health exposure system to allow for recharging or augmentation of the power source provided as a component of health exposure monitoring system.

18. The health exposure system of claim 1, wherein the system is sized and configured to be unobtrusively worn on the person or apparel of a user.

19. A method of operating a health exposure sensor system, the health exposure sensor system comprising: a monitoring platform which comprises at least one modular gas sensor, a circuit board comprising a main microcontroller, and an array of data ports for connecting the at least one modular gas sensor to the circuit board; wherein each modular gas sensor comprises:
- a gas detector enclosed in a sensor housing with an opening for gas diffusion to the gas detector; and
- a gas sensor circuit board comprising a gas sensor microcontroller, wherein the gas sensor microcontroller comprises at least one on-chip universal asynchronous receiver-transmitter (UART) peripheral and at least one on-chip USB peripheral, wherein both each UART peripheral and each USB peripheral comprise input/output (I/O) functionality and are connected to a single data port interface for communication external to each modular gas sensor;

the method comprising: selectively enabling individually via digital I/O configuration of the gas sensor microcontroller either each UART peripheral or each USB peripheral.

20. The method of claim 19, wherein each UART peripheral is enabled for communication internally within the health exposure sensor system.

21. The method of claim 19, wherein each USB peripheral is enabled for communication with a USB device external to the health exposure sensor system.

* * * * *